US005522805A

United States Patent [19]
Vancaillie et al.

[11] Patent Number: 5,522,805
[45] Date of Patent: Jun. 4, 1996

[54] SURGICAL FLUID MONITOR

[75] Inventors: Thierry G. Vancaillie, San Antonio, Tex.; Robert K. Mitchiner, Longmont; David W. Newton, Boulder, both of Colo.

[73] Assignee: Aquintel, Inc., Mountain View, Calif.

[21] Appl. No.: 484,877

[22] Filed: Jun. 7, 1995

Related U.S. Application Data

[63] Continuation-in-part of Ser. No. 237,350, May 3, 1994, Pat. No. 5,492,537.

[51] Int. Cl.⁶ ..................................................... A61M 5/00
[52] U.S. Cl. ........................... 604/246; 604/65; 128/760
[58] Field of Search ..................................... 604/65–67, 31, 604/4, 246; 128/760, 766; 364/413.01, 413.02

[56] References Cited

U.S. PATENT DOCUMENTS 4,449,538  5/1984  Corbitt et al. .
4,995,268  2/1991  Ash et al. .
5,135,485  8/1992  Cohen et al .

*Primary Examiner*—Randall L. Green
*Assistant Examiner*—Perry E. Van Over
*Attorney, Agent, or Firm*—Akin, Gump, Strauss, Hauer & Feld

[57] ABSTRACT

A monitor to provide substantially real-time estimates of fluid absorbed by a patient during an endoscopic surgical procedure. The monitor comprises means for weighing fluid administered to the patient intravenously, as well as that introduced through the endoscope for irrigation purposes. In addition, means are provided for weighing fluid recovered from the patient, the endoscope, and the surgical drapes. The total weight of fluid administered, reduced by subtracting the total weight of fluid recovered, comprises the calculated fluid absorbed. Through manual entries and/or switch settings, computing means maintain totals of fluid administered and fluid collected even as fluid sources are replaced and the fluid collector is emptied. Optional verticality compensation means and anti-rotation devices are included.

15 Claims, 12 Drawing Sheets

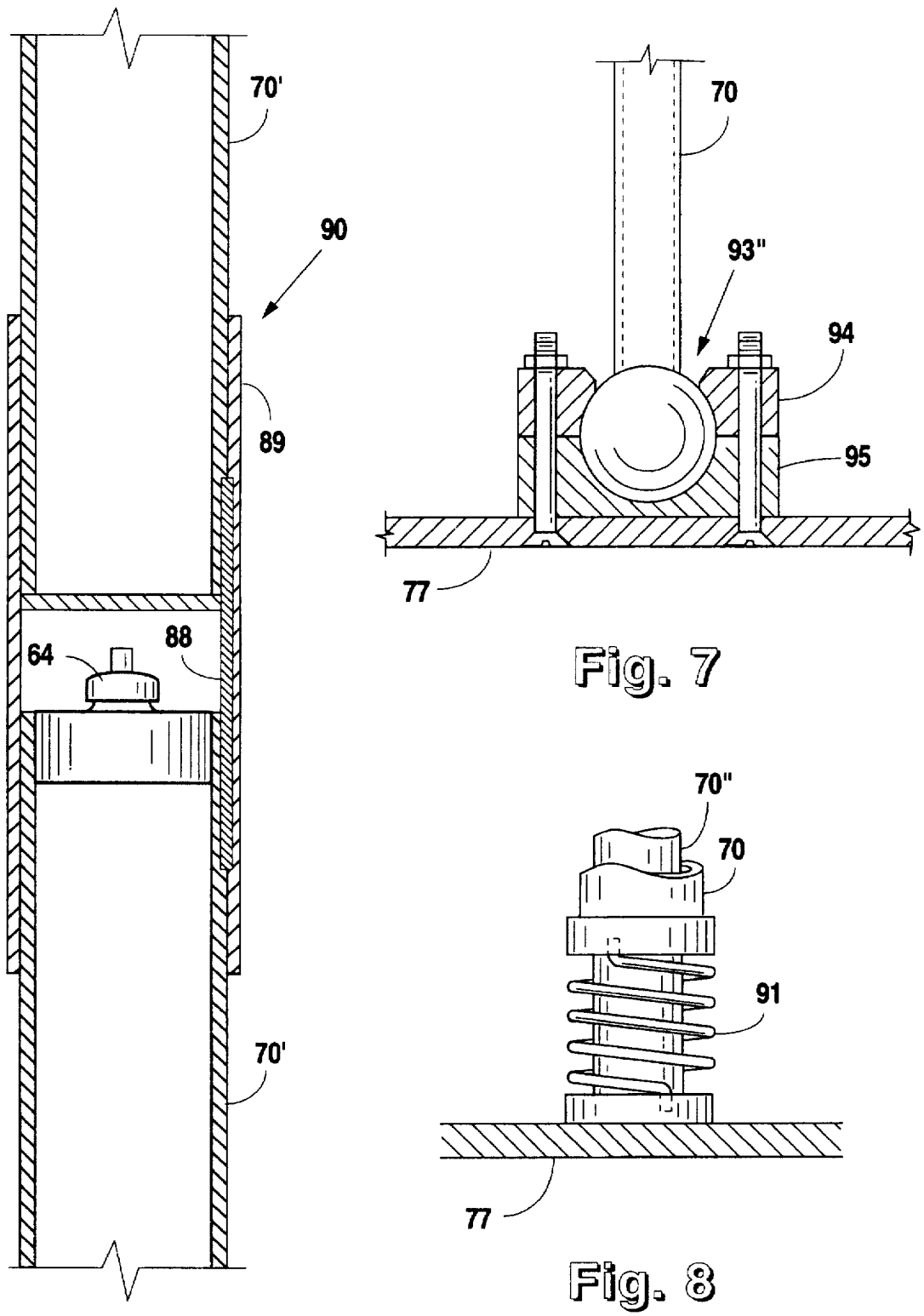

SURGICAL FLUID MONITOR

CONTINUATION INFORMATION

This application is a continuation-in-part of application Ser. No. 08/237,350 filed 3 May 1994 now U.S. Pat. No. 5,492,537.

BACKGROUND

1. Field of the Invention

The invention relates to methods and apparatus for estimating the volume of fluid absorbed by a patient during a surgical procedure.

2. Fluid Absorption in Endoscopic Surgery

Endoscopic surgery is frequently performed on the uterus (transvaginally) and the prostate gland (transurethrally). These anatomic approaches generally require that an endoscope be inserted through an orifice into a body cavity and that excised tissue be removed from the surgical site through the same orifice. To maintain the surgeon's clear view of the surgical site and to facilitate continuous removal of blood and small tissue fragments, a substantially continuous flow of relatively low-pressure (frequently electrically non-conducting) irrigation fluid from an external reservoir is maintained through the endoscope. The fluid is frequently formulated as a substantially isosmotic crystalloid solution comprising one or more nonelectrolytes such as glucose, urea, glycine, mannitol, or sorbitol. Pressurization of the fluid often results in mild local distention of tissues, which can lead to absorption of a portion of the fluid through surgical lesions.

It is recognized that incidental absorption of relatively small quantities of irrigation fluid is virtually unavoidable during endoscopic surgery and that for most patients the clinical importance of such small quantities would be negligible. But certain patients (for example, those in heart or renal failure) may be particularly sensitive to the changes in intravascular volume that absorption of even small quantities of irrigation fluid can cause. And absorption of larger quantities may well have adverse clinical consequences even in normal patients.

For example, if irrigation fluid under a pressure head of approximately one meter is applied to the urethra and bladder of an adult patient undergoing transurethral resection of the prostate (TURP), one may estimate that about 10 to 30 ml of irrigation fluid will be absorbed per minute of resection time. On the other hand, the absorption of as much as 6 to 8 liters of irrigation fluid has been documented during TURP's extending over a period of 2 hours. Following absorption of such large amounts of irrigation fluid, dilutional hyponatremia and/or over-hydration may be manifest in seizures, coma and death.

In part, this is because a patient may retain only 20% to 30% of absorbed irrigation fluid within the intravascular space. Free water generally moves to the interstitial space, where it may substantially increase the likelihood of pulmonary and cerebral edema formation. Whether or not a given patient will actually develop pulmonary and cerebral edema, however, depends on several factors, including that patient's cardiovascular status, the amount and rate of onset of the irrigation fluid load, the initial fluid volume status of the patient, and the amount of blood loss during the operation.

Thus, careful monitoring of fluid intake by the patient in real time may be very helpful when combined with other preoperative and interoperative assessments. Note that calculation of the total fluid intake by a patient during an endoscopic surgical procedure includes irrigation fluids (having no electrolytes) and intravenous fluids (which may or may not contain electrolytes). Nonelectrolyte fluids administered intravenously may occasionally represent a clinically significant fraction of the total free water intake. When this occurs, the intravenously administered free water volume should be added to an estimate of irrigation fluid absorbed.

Measurement of fluid infused through an intravenous catheter is relatively easy, although subject to about 10% reading error in collapsible plastic bags. In contrast, estimation of irrigation fluid absorption is error-prone because irrigation fluid may drain continuously from both the endoscope and the body orifice in which it is inserted (i.e., the vagina or urethra as the case may be). Draining fluid is commonly distributed over the surgical drapes, the operating table and floor, as well as to containers resting on the floor. Incidental absorption by and adsorption to various operating-room surfaces, as well as losses in handling due to spillage and splashing, make irrigation fluid recovery uncertain. This reduces the clinical usefulness of fluid absorption estimates.

Nevertheless, because the complications of excessive intravascular volume expansion and/or serious free water overload can be lethal to the patient, the surgeon must have sufficient warning of trouble to take corrective action. Such warning may be provided by having operating room personnel monitor the amount of non-electrolyte intravenous fluid and irrigating fluid drawn from source bags on an IV stand and subtract the amount of irrigation fluid collected from the endoscope drain and surgical drapes. As the procedure progresses, comparisons of the volume remaining in the source bags relative to the volume collected provides an estimate of absorbed fluid volume. Because some of the irrigation fluid is inevitably lost, the estimate of absorbed fluid will tend to be high, thus providing an earlier warning than if actual measurements of absorbed fluid were available. This safety margin may be reduced or eliminated, however, if reading errors are taken into account. For example, the tolerance on fluid volume measurements in the supply bags is about ±10%, so for each three liter source bag, the error band may be about 600 ml wide.

A more convenient and more accurate method that has been proposed requires hanging the source bags and a collector bucket on the same spring scale and by that means directly and automatically comparing a decrease in source fluid weight with an increase in collected fluid weight. This suspended system, while simple, is inconvenient because it is fixed to a support in the ceiling. Additionally, such a suspended system may has a tendency to rotate around the suspension member, kinking source and/or drainage tubes and complicating weight measurements because of varying lateral and vertical load components. Accurate weights can only be obtained if the suspended system is actually vertical, but in general it will not be because of the lateral forces applied by the various fluid lines attached to it. Finally, errors inherent in accounting for fluid source bags added to the scale and fluid drainage removed from the collector make use of a suspended system in elective surgery problematical.

SUMMARY OF THE INVENTION

The present invention answers the need for apparatus and methods to provide substantially real-time estimates of irrigation fluid absorbed by a patient during an endoscopic surgical procedure. Using the present invention, an estimate of fluid absorbed by a patient is obtained by subtracting an estimate (based on weight) of irrigation fluid recovered during the surgical procedure from an estimate (again based on weight) of fluid administered during the surgical procedure. Weight-based fluid volume measurements, made on command or automatically, obviate errors inherent in any manual recording or reading of scales. The result is greater clinical reliability when compared to conventional methods of fluid monitoring.

In free-standing embodiments, the invention incorporates at least one anti-rotation device to eliminate tangling of fluid supply and drainage tubes. Certain free-standing embodiments provide an adjustable floor-mounted stand or a ball-joint mount to ensure that the main fluid support column is vertical, while other embodiments employ level sensor measurements to facilitate compensation for measurements of fluid weight made when the fluid support column is off-vertical.

The invention comprises a surgical fluid monitor, the monitor in turn comprising weight-sensitive fluid source support means (for example, hooks) for simultaneously suspending and weighing one or more fluid sources individually (that is, allowing individual measurement of the weight suspended from each fluid source hook) or collectively (that is, yielding the sum of weights suspended from a plurality of fluid source hooks). Further, one or more waste fluid collectors are simultaneously weighed, optionally in combination with the fluid source(s). In the latter case, because a single weight measurement reflects the combined weight of all fluid sources and waste fluid collectors, the weights of individual components is obtained, if desired, by removing the component in question and noting the decrease in collective weight.

The surgical fluid monitor may comprise, for example, one or more fluid source hooks mounted on a wall or on a fluid support column which itself is fixed (as by welding or bolting) to a platform or equipment cart movable over the floor. The platform or cart preferably has retractable wheels or extendable legs which facilitate stable positioning in a desired floor location. Fluid source hooks mounted on a wall, for example, are necessarily inherently weight-sensitive (that is, they comprise at least one weight-sensitive element), but fluid source hooks mounted on a fluid source column may be inherently weight-sensitive, or may be weight-sensitive only in the sense that the column comprises at least one weight-sensitive element.

In use, fluid-containing bottles, plastic bags, or similar containers are suspended from one of the fluid source hook(s) to hang substantially freely. Preferred embodiments of weight-sensitive fluid source hooks comprise one or more (preferably solid-state) force-sensitive devices, each producing a signal indicative of the weight applied to a single hook. Alternatively, a single force-sensitive device may also be employed (for example, within the fluid support column) to produce a signal indicative of the weight applied to all column-supported fluid source hooks collectively. In either of the latter two cases, a separate force-sensitive device would preferably be employed to produce a signal indicative of the weight of waste fluid collected, either as a separate signal or combined with the weight of fluid sources supported by a fluid support column.

For convenience, waste fluid will commonly be distributed into a plurality of collection containers which will be weighed collectively. If the collection containers are suspended from the surgical fluid monitor's fluid support column and if all fluid sources are also supported by the column, a single force-sensitive device may be used to produce a signal indicative of the combined weight of all irrigation fluid sources and of all waste irrigation fluid containers collectively. Declines in the indicated collective weight may be considered a conservative estimate (that is, an over-estimate) of the weight of fluid absorbed by the patient.

In preferred embodiments of the invention, each force-sensitive device comprises a solid-state load cell (comprising e.g., a piezoelectric or strain gage force sensor). Fluid support means thus produce a source weight signal indicative of fluid source weight, the signal eventually being coupled to computing means by coupling means which include one or more insulated electrical conductors and/or wireless means (including a radio transmitter and receiver or, preferably, an infrared transmitter and receiver). In the latter case, the infrared transmitter for the signal indicative of a fluid source weight may preferably be battery-powered.

In certain embodiments, the force-sensitive device does not sense the full weight of fluid supported by the fluid support means. This may occur, for example, if a platform-mounted fluid support column is placed on an uneven or sloping floor where the platform would not be substantially level. If the non-level platform causes the fluid support column to be non-vertical, then a component of the fluid weight vector will not be coaxial with the column. The non-coaxial weight vector may then be resolved into an axial component (creating a reduced axial compressive stress in the column) and a transverse component (creating transverse or shear stress in the column). The reduced axial compressive stress is obtained by multiplying the axial compressive stress that would be present if the column were vertical by the cosine of the angular deviation of the column from vertical. Since the force-sensitive device responds substantially to axial stress, the indicated weight on the pole will always be less than the true weight unless the pole is vertical. For small deviations from vertical, the errors in indicated weight will be relatively small, but they will be systematic (i.e., always increasing as additional fluid sources are supported by the column).

The present invention comprises methods and apparatus to eliminate and/or compensate for the above verticality errors. For example, if the platform-mounted column is configured with a verticality adjustment, the pole can be made substantially vertical even if the platform is not level. In preferred embodiments, the verticality adjustment comprises a ball-joint column mount in which the column can be positioned vertically either manually or automatically, being held in place with a plurality of manually or automatically adjusted mechanical stops (such as screws). Such a ball-joint support may be relatively close to the column platform at the lower end of the pole, or sufficiently elevated so that the center of gravity of the column, force-sensitive device, fluid source(s) and waste fluid container(s) is lower than the ball-joint support point. In the latter configuration, the column will be free to behave as a pendulum and will maintain a substantially vertical orientation within its range of motion in the absence of significant eccentric vertical loads.

Yet another approach to the verticality problem with a platform-mounted column is to allow the column to maintain a non-vertical position while measuring the degree of deviation from the vertical and using the measured deviation and reduced axial force to calculate the true weight of one or more fluid sources and/or waste fluid containers.

Waste fluid containers have a relatively large capacity (preferably about 3 fluid liters) in certain embodiments to obviate frequent emptying of the container during a surgical procedure. Because each such container weighs more than 3 kilograms when full, even small verticality errors may cause clinically significant errors in fluid volume estimates. The container is substantially sealable and has a vacuum port (to be connected to a vacuum pump) to facilitate establishment of a partial vacuum within the container which will tend to draw irrigation fluid in through the port(s) provided in the container. One or more fluid collector containers are preferably supported by the fluid support column, which in turn is supported on a weight-sensitive fluid support comprising a force-sensitive device which produces a signal indicative of the total weight applied to the fluid support column. The fluid collector weight signal may be obtained from the total weight value by subtracting the weight of any fluid sources also supported by the column. Where a separate determination of fluid source weight supported by the fluid support column is not made, the total fluid support column weight value is observed for reductions indicative of a difference between the weight of source fluid leaving the column support and the weight of waste fluid returning to the column support. A conservative approach to patient management would mean that a substantial portion of the difference weight (perhaps all of it) represents irrigation fluid absorbed by the patient. The attending physician, having previously formed an opinion on how much irrigation fluid the patient could safely absorb, will be warned when the difference weight value substantially equals this predetermined amount of fluid.

The fluid source and fluid collector weight determinations can be read and subtracted manually as indicated above, or computing means coupled to the fluid source weight signal and the fluid collector weight signal may calculate a difference weight value. The computing means is preferably a digital computer comprising a processor, a memory, a keyboard or analogous manually actuated device for entry of data and instructions, and an input-output section.

The display signal is transmitted to display means, which are thus coupled to the computing means for transducing the display signal for human observation. The display means may comprise a computer screen and/or a digital readout. In preferred embodiments, the computing means may transmit the display signal in, for example, ASCII code to a commercially available digital readout device capable of decoding and displaying ASCII-coded signals. Several such devices are available through commercial electronics parts distributors and, while not further described herein, are well-known to those skilled in the art. Note that intermediate values of variables obtained in the course of producing the calculated fluid absorbed value may also be displayed as desired.

As noted above, preferred embodiments of the surgical fluid monitor include a vacuum connection to the fluid collector container to facilitate maintenance of a partial vacuum within the container in use. The partial vacuum, in turn, facilitates entry of waste irrigation fluid into the container from sources including the endoscope drain, a drain from a floor sump or fluid-trapping floor mat, and a drain configured to recover irrigation fluid which splashes on the operating table or which emerges from a vagina or urethra (with the patient in the lithotomy position). Additionally, the fluid collector container may comprise a filter or strainer intended to separate small pieces of tissue from one or more incoming streams of waste irrigation fluid, as well as a bunghole and/or stopcock to facilitate emptying the container.

BRIEF DESCRIPTION OF THE DRAWINGS

FIG. 6 schematically illustrates an in-line force-sensitive device.

FIG. 7 schematically illustrates a ball-joint support for a fluid support column.

FIG. 8 schematically illustrates a spring support for a fluid support column.

DETAILED DESCRIPTION

Figure 12A:
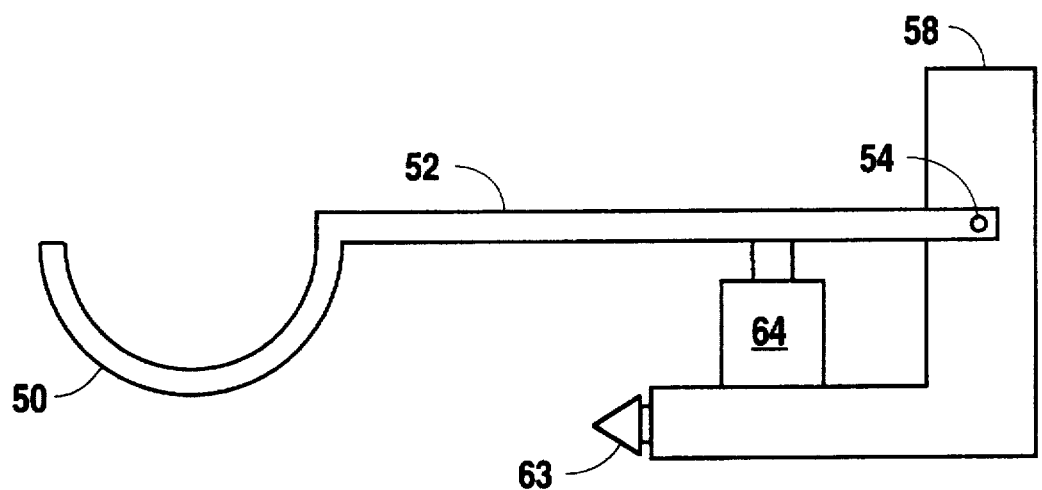
FIGS. 12A–E schematically illustrate alternative preferred embodiments of weight-sensitive fluid supports.
Figure 12B:
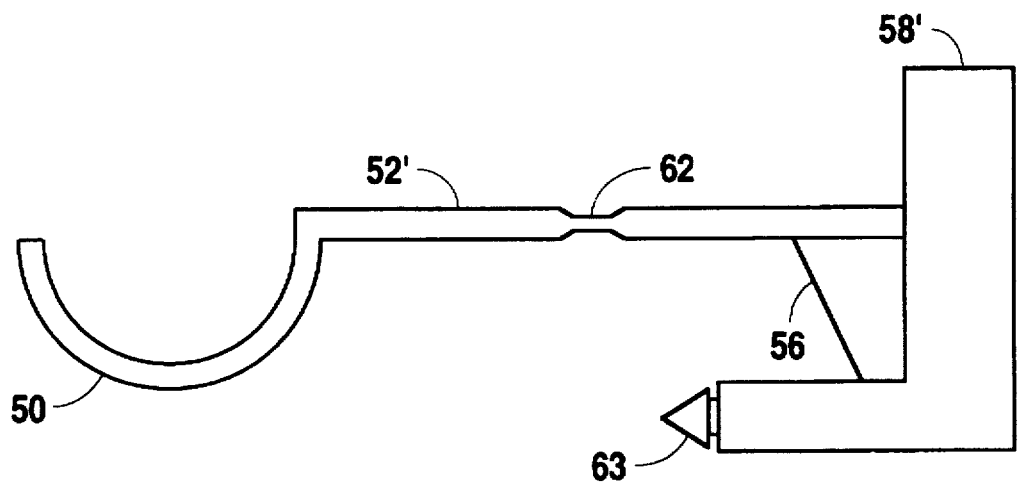
Figure 12C:
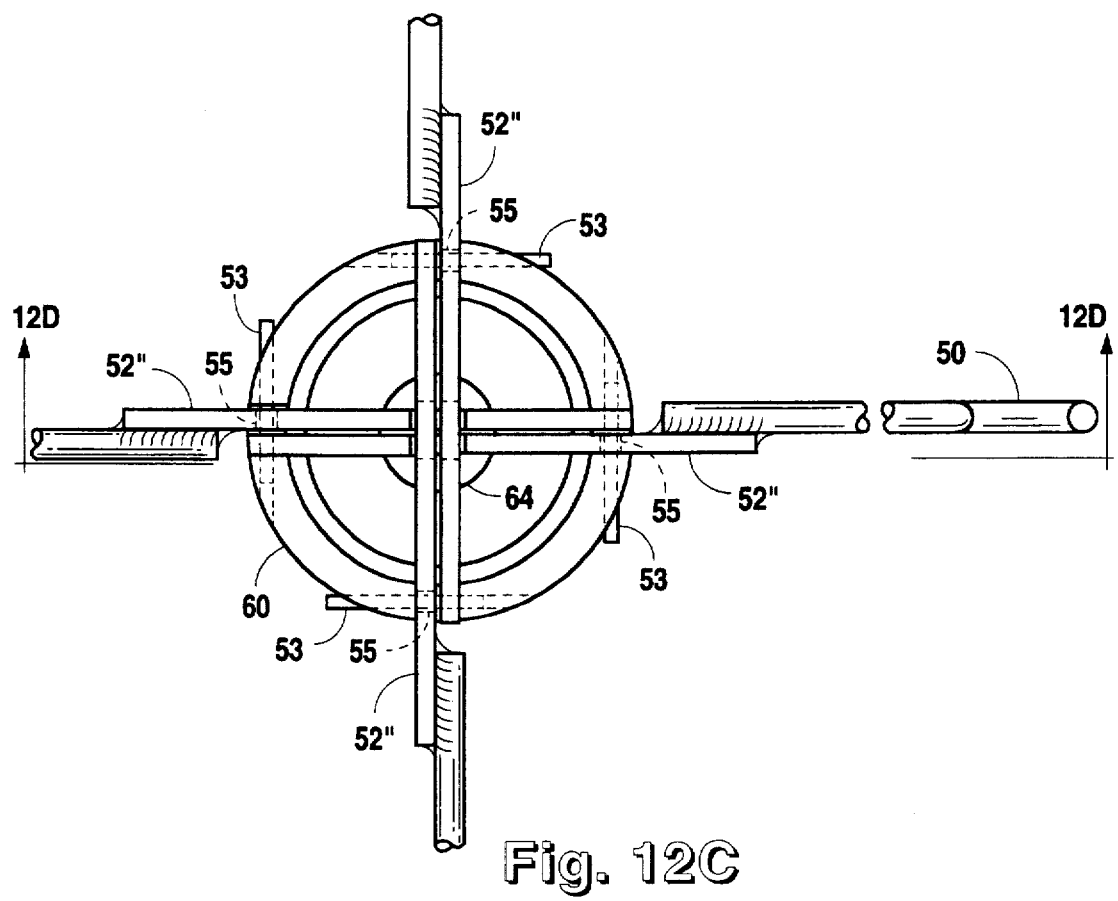

FIGS. 1–5 schematically illustrate preferred embodiments of portions of a surgical fluid monitor comprising verticality compensation means and anti-rotation devices. The fluid support column 70, 70' may comprise a plurality of passive fluid source hooks 50 (that is, hooks without inherent weight-sensing capability). Alternatively, column 70, 70' can have no fluid source hooks at all, or one or more weight-sensing hooks as schematically illustrated in FIGS. 12A–C (that is, hooks comprising one or more force-sensitive devices such as a piezoelectric sensor 64 or a strain gage sensor 62). The height of fluid source hooks, if present, may be manually adjusted by sliding member 70' in or out of member 70 and temporarily fixing the height of column 70, 70' with thumb screw 71.

Figure 2:
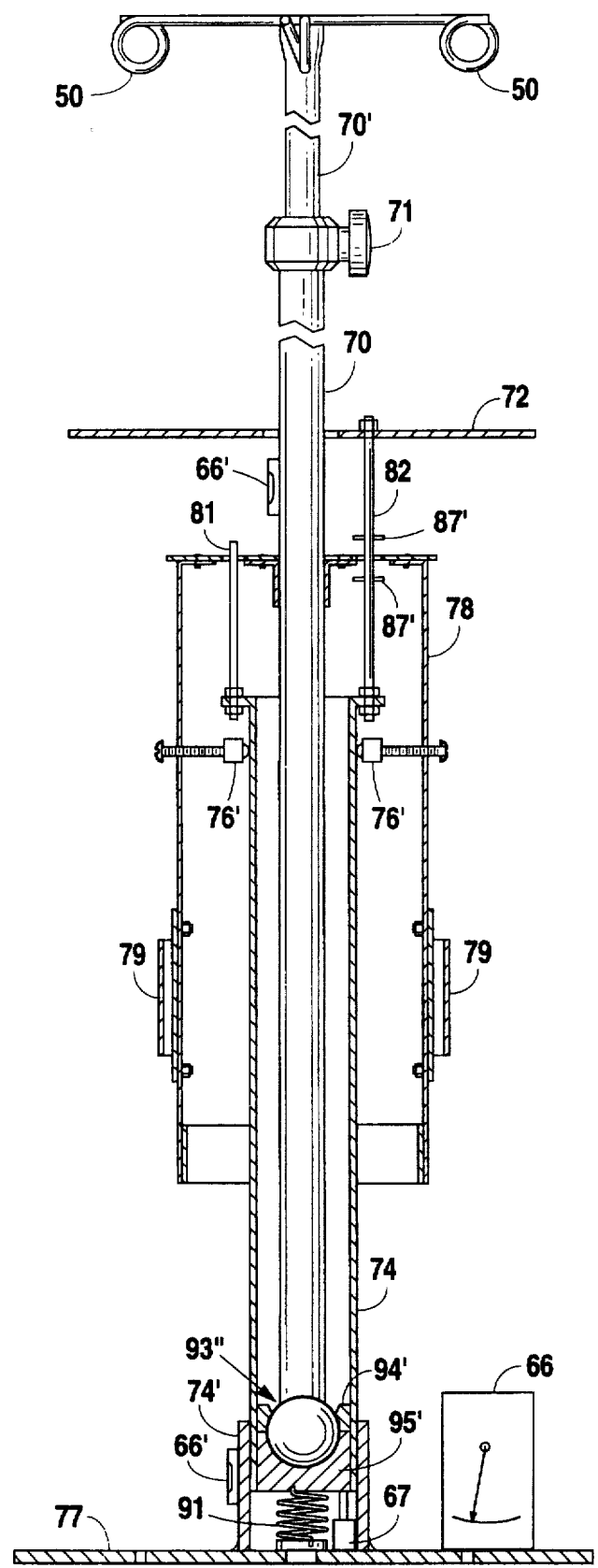
FIG. 2 schematically illustrates a preferred arrangement for source fluid supports and fluid collector supports on a ball-joint fluid support column with verticality adjustment which bears on a single weight-sensitive element.
Figure 3:
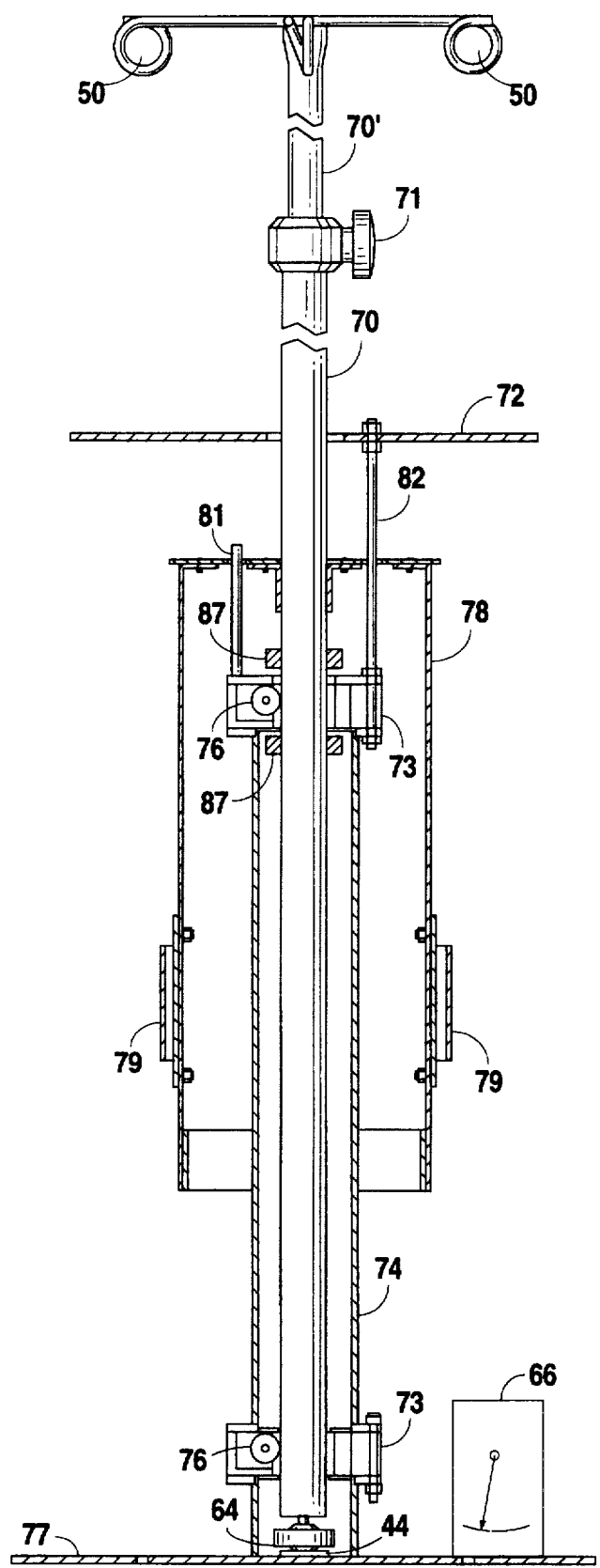
FIG. 3 schematically illustrates a preferred arrangement for source fluid supports and fluid collector supports on a fluid support column having a verticality sensor and bearing on a single weight-sensitive element.
Figure 4:
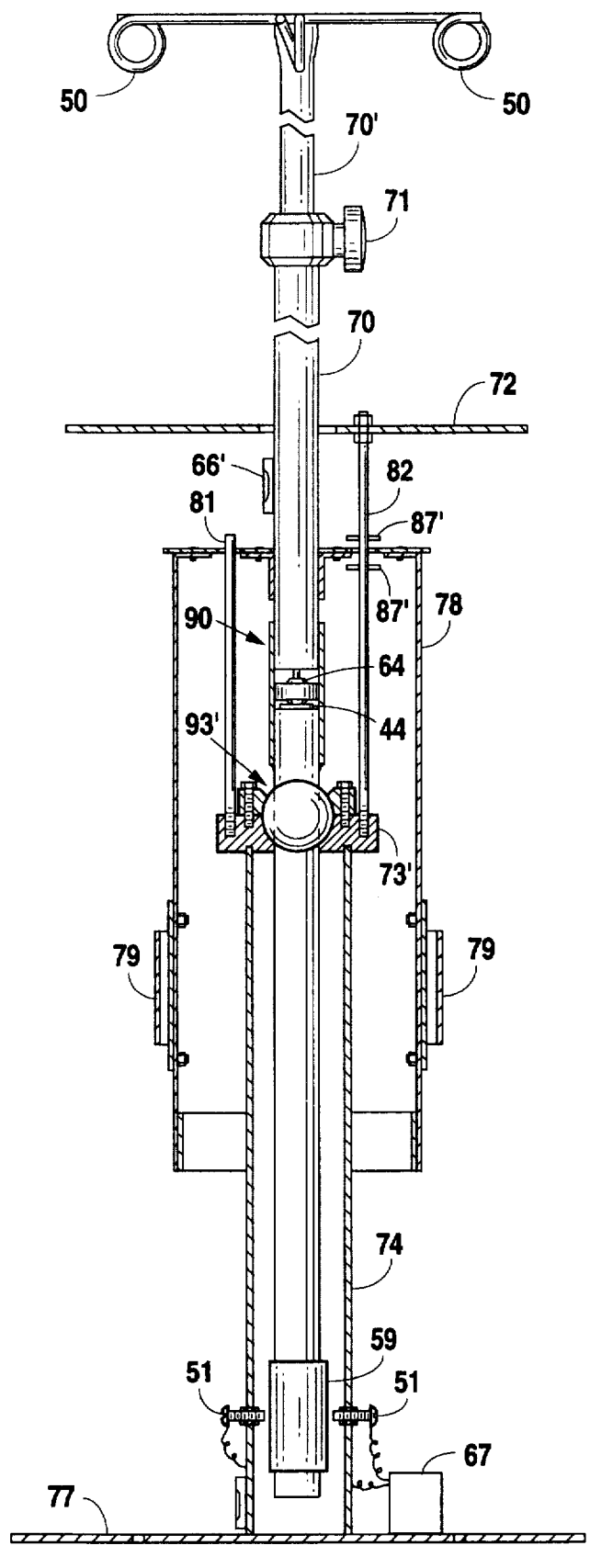
FIG. 4 schematically illustrates a preferred arrangement for source fluid supports and fluid collector supports on a ball-joint supported pendulous fluid support column bearing on a single weight sensitive element.
Figure 5:
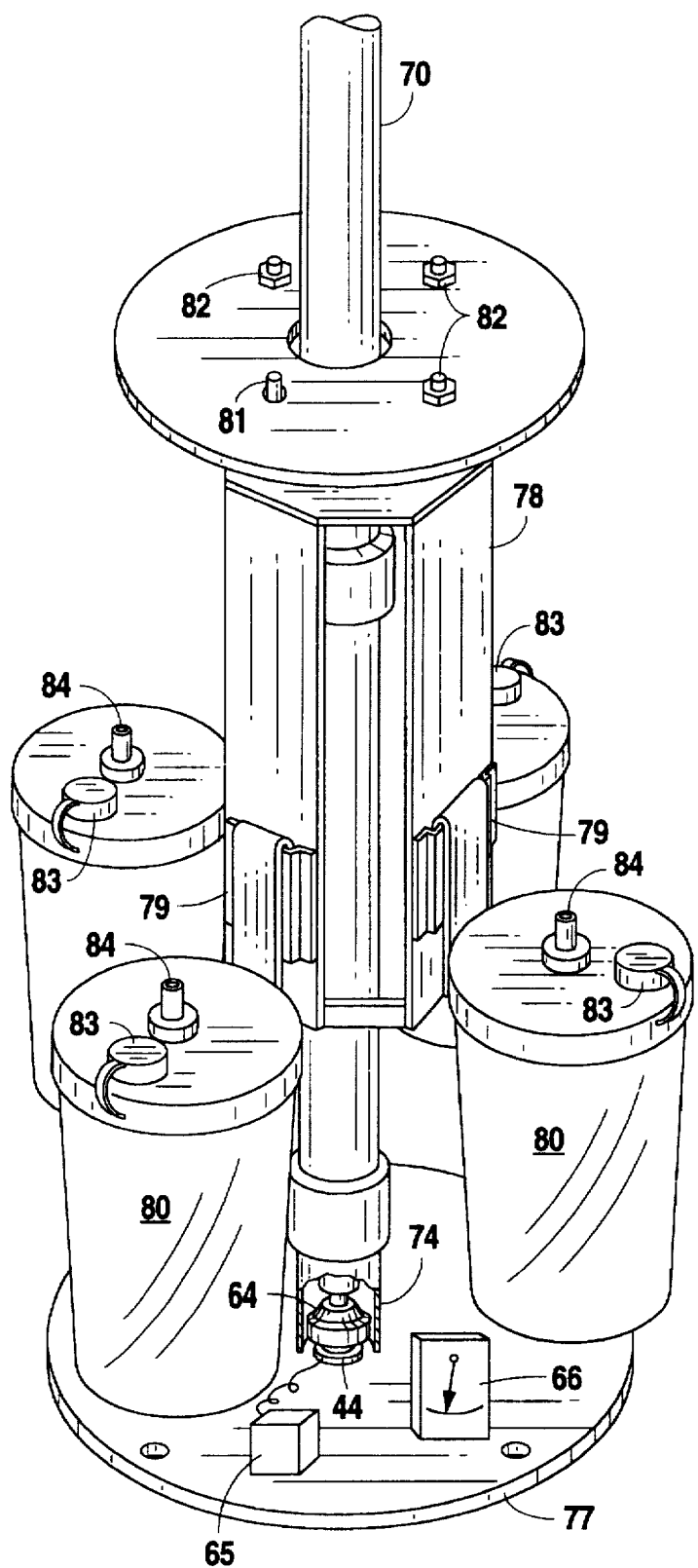
FIG. 5 schematically illustrates a preferred arrangement for fluid collector supports on a fluid support column bearing on a single weight sensitive element.

In each of the FIGS. 1–5, a platform-mounted support sleeve 74 is firmly fixed to a base plate 77 (as by welding), with base plate 77 intended to rest directly on a floor or on (retractable or lockable) casters or legs (not shown). Optional shelf 72 is coupled (as by stand-off bolts) to support sleeve 74, and shelf 72 does not contact column 70, 70' in use. Shelf 72, when present, is supported by standoff bolts 82 which, like anti-rotation pin 81, are fixed to support sleeve 74 through bearing block 73 (FIGS. 1 and 3), through a flange of sleeve 74 (FIG. 2), or ball-joint socket block 73' (FIG. 4). Block 73' serves part of the purpose of bearing block 73 (capping sleeve 74 and anchoring anti-rotation pin 81 and stand-off bolts 82) as well as providing a socket bearing as in ball-joint socket blocks 95,95' (see FIGS. 8 and 2). Wherever ball-joint sockets are found in the illustrated embodiments, the ball is retained in the socket bearing by a ball retainer 94,94'. Note that the ball-joint socket of FIG. 7 illustrates a portion of an embodiment wherein a terminal ball-joint 93" is directly mounted on base plate 77. The configuration of FIG. 7 contemplates use of one or more in-line force-sensitive assemblies 90 in fluid support column 70,70' (see FIG. 4), although the entire embodiment is shown.

Figure 1:
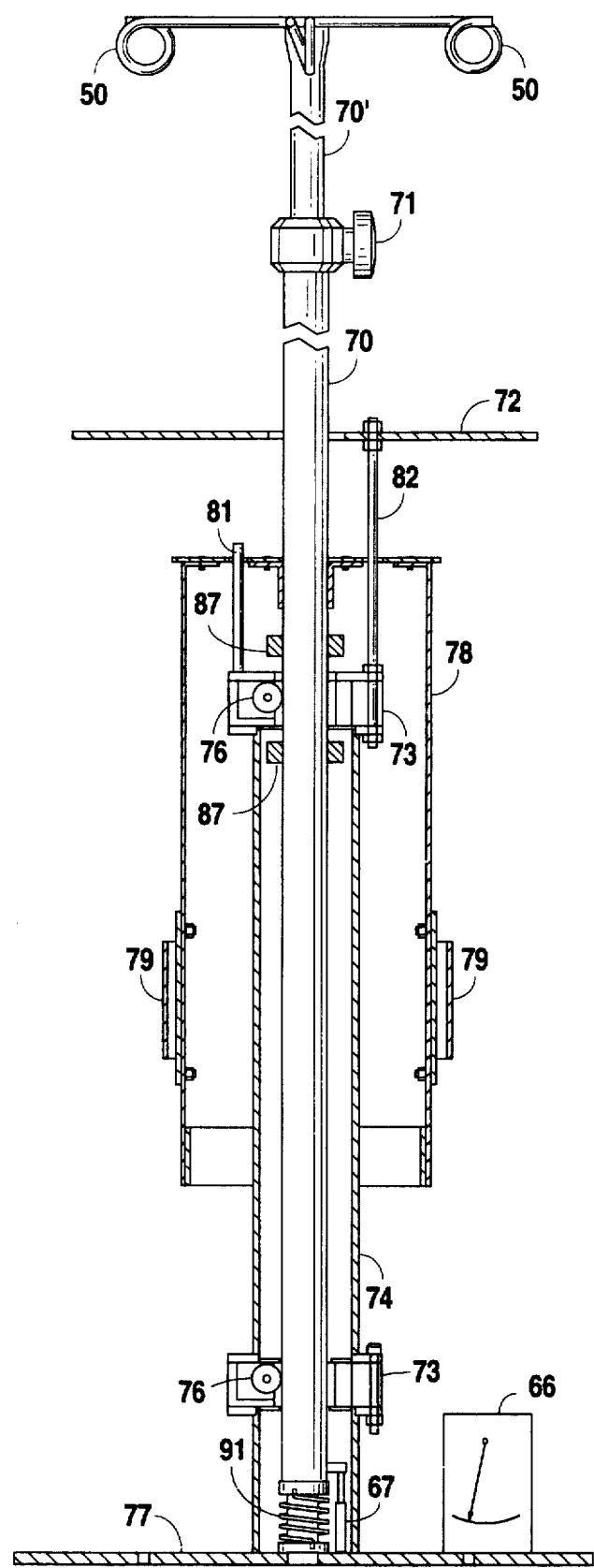
FIG. 1 schematically illustrates a preferred arrangement for source fluid supports and fluid collector supports on a fluid support column bearing on a single weight sensitive element.

Anti-rotation pin 81 passes through an enlarged hole in collector support frame 78, thereby preventing frame 78 and column 70,70' from rotating excessively with respect to pin 81, support sleeve 74 and base plate 77. Additional anti-rotation devices schematically illustrated in the drawings include the optional in-line force-sensitive assembly 90 (comprising load cell 64, in-line sleeve 89, and spline 88), and the anti-rotation support spring 91 (FIGS. 1, 2 and 8). Note that support spring 91 may be used without an internal guide (see FIG. 2), or with an internal guide 70" (see FIG. 7) over which it slides and which will tend to stabilize spring 91.

Collector support frame 78 is supported by column 70,70' and in turn supports waste fluid collectors 80 via collector brackets 79. Waste fluid enters collectors 80 via inlet ports 83 (capped when not in use) assisted by vacuum applied via vacuum ports 84. The weight of fluid collectors 80 is carried by support frame 78, which is itself supported by fluid support column 70,70'. Column 70,70', in turn, is supported by at least one weight-sensitive device. In FIGS. 1 and 2, the weight-sensitive device comprises spring 91 and means to measure spring 91 compression and/or expansion (for example, a linear variable differential transformer (LVDT) 67 coupled around spring 91 substantially as shown). In FIGS. 3 and 4, the weight-sensitive device comprises a load cell 64 (the load cell itself comprising, for example, a piezoelectric load sensor). Note that travel of fluid support column 70,70' which compresses or expands spring 91 is preferably limited to prevent damage to spring 91 and/or to LVDT 67. This travel limitation may, for example, be via stop rings 87 adjustably fixed (as by set screws) to member 70 (see FIGS. 1 and 3). Analogously, travel limitation to prevent damage to load cell 64 may be via stop pins 87' adjustably fixed to stand-off bolts 82 as through one of a plurality of transverse holes in bolts 82 (see FIGS. 2 and 4).

Note that the compliance (or compression per unit load) for a spring 91 will in general be significantly greater than the compliance for a load cell 64. Thus, stop rings 87,87' in the embodiments of FIGS. 3 and 4 will preferably be set with smaller clearances than the analogous settings for the embodiments of FIGS. 1 and 2. If load cell 64 were directly mounted, for example, between column 70,70' and base plate 77, a clearance of only a few thousandths of an inch might be necessary to prevent compressive damage to the load cell. Such a small clearance would impose substantial costs in manufacturing and is preferably obviated by inclusion of a shock-absorbing spacer 44 (comprising, for example, a rubber washer or substantially flat spring) mounted in-line with the load cell 64 and its supported load. Inclusion of a shock-absorbing spacer 44 in-line with load cell 64 effectively increases the compliance of load cell 64 and thus allows the setting of wider limits on travel limitations for column 70,70'.

Note also that travel of fluid support column 70,70' as described above is facilitated by one or more sleeve or roller bearings in the schematically illustrated embodiments of FIGS. 1–3 (roller bearings 76,76') and of FIGS. 2, 4 and 6 (the sleeve bearing formed by ball-joint socket block 95' sliding within support sleeve 74, and the sleeve bearing formed by member 70' of in-line force-sensing assembly 90 sliding within splined sleeve 89 guided by spline 88). In FIG. 2, the external base sleeve 74' serves not as a bearing surface but to provide additional space for spring 91 and coupled LVDT 67.

Fluid support column 70,70' may be adjusted to be vertical or may be allowed to tilt off-vertical in embodiments with a sufficiently large base plate 77 to prevent significant instability. FIGS. 2 and 4 schematically illustrate two verticality compensation means in which fluid support column 70,70' is rotated within a ball joint 93', 93" to achieve verticality as indicated by verticality sensor 66' on the column 70,70'. Verticality sensor 66' is a column-mounted version of verticality sensor 66 which is schematically shown as indicating tilt of base plate 77 in FIGS. 1–3 and 5. Sensors 66, 66' may be bulls-eye bubble levels or analogous pendulous sensors well-known in the art for indicating tilt about any horizontal axis (the sensors preferably producing an electrical signal indicative of such tilt).

Fluid support column 70,70' may be adjusted to be vertical by rotation about an end-mounted ball joint 93' with thumbscrew-mounted bearings 76', or it may be allowed to hang vertically (pendulously) while supported in ball joint 93'. In the latter case, a sufficiently heavy weight 59 must be placed below ball joint 93' to insure that the center of gravity of the entire fluid support column 70,70' (including all fluid sources and waste fluid containers) is below ball joint 93'. Note that for the pendulous column, eccentric loading will tend to cause an off-vertical condition. This condition can be indicated by the verticality sensor 66' or by contact of the pendulous fluid support column with previously adjusted thumbscrew-mounted electrical switch contacts 51 which can be made to light a bulb, ring a bell or otherwise signal an alarm in junction box 67.

For the pendulous fluid support column of FIG. 4 having an in-line force-sensitive assembly 90, the output signal of force-sensitive device (load cell) 64 includes the true weight of the source fluids and waste fluids supported by the column, while the output signal of load cell 64 in FIG. 3 or of the linear variable differential transformer 67 in FIGS. 1 or 2 (which measures weight-induced compression of anti-rotation support spring 91) will include only a reduced indication of the true weight of supported fluid (that is, the true supported weight multiplied by the cosine of the off-vertical angle of support sleeve 74. When using the embodiments of FIGS. 1–3, the true weight may be obtained by measuring the off-vertical tilt of support sleeve 74 with level sensor 66 and dividing the indicated weight by the cosine of the off-vertical tilt angle.

Thus, verticality compensation means can provide, true indications of changes in the fluid weights supported by fluid support column 70,70' by making the column (and the sensitive axis of the force-sensitive device) substantially vertical, or by measuring the degree of off-vertical tilt in the column and using that information to calculate true weights from indicated weight values.

Figure 11:
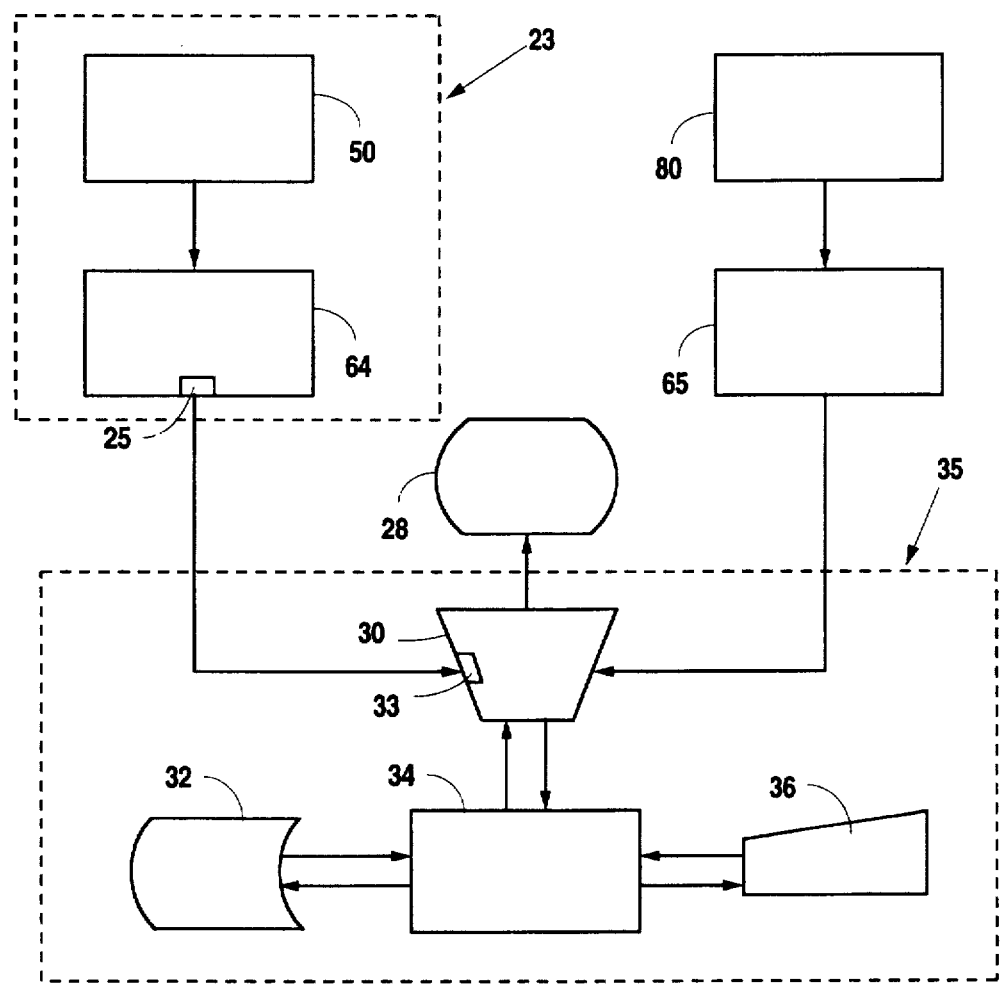
FIG. 11 schematically illustrates the flow of signals in a preferred embodiment of the invention.

In certain embodiments, the above measurements and calculations can be made automatically according to a predetermined program. Referring to FIG. 11, the signal flow in a preferred embodiment of the invention involving separate measurement of source and waste fluid weights can be seen to originate in part from the weight-sensitive fluid support means 23 which comprises (see FIGS. 12A–C, for example) a source fluid support hook 50 coupled to a weight-sensitive device 64 (e.g., a solid-state load cell). Signal flow in FIG. 11 also originates from fluid collectors 80 acting on an irrigation fluid collector weight sensor combination 64, 65 (see FIG. 5). Note that in an alternative embodiment, one or more fluid collectors 80 may also be placed on a commercially available electronic scale (not shown) comparable to those used for weighing patients and having a signal output analogous to that of weight sensor combination 64,65. Fluid source weight signals from weight-sensitive device 64 are directed by coupling means including one or more insulated electrical conductors and/or wireless transmitter 25 (which may include, e.g., infrared transmitter 63 in FIGS. 12A,12B) to the input-output section 30 of computing means 35 (which in preferred embodiments may be configured to receive signals transmitted by insulated electrical conductor(s) and/or to receive wireless (e.g., radio or infrared) signals from wireless transmitter 25 with wireless receiver 33. Flow of signals through input-output means 30 to processor 34 and memory means 32 is controlled by processor 34 using instructions stored in memory means 32 and/or instructions from manual input device 36. Processor 34 preferably computes a calculated fluid absorbed value according to a method analogous to or substantially identical to that illustrated schematically in FIG. 4, directing the signal representing the calculated fluid absorbed value through input-output means 30 to display means 28.

Memory means 32 may comprise, for example, magnetic tape, magnetic disks, or non-magnetic solid-state devices (e.g., optoelectronic memory or solid state switches). Manually actuated input device 36 may comprise, for example, magnetic cards, punched cards, paper or magnetic tape, a key board, or one or more switches. Processor 34 and input-output means 30 may take the form, in preferred embodiments, of the analogous sections of a personal computer, as may display means 28. However, display means 28 may comprise in addition to or in place of a computer display screen a digital readout device and/or an auditory indication of the calculated fluid absorbed value and/or auditory signals indicating when the calculated value has exceeded a limit previously stored in memory means 32 or entered into processor 34 through manual input device 36.

Figure 12D:
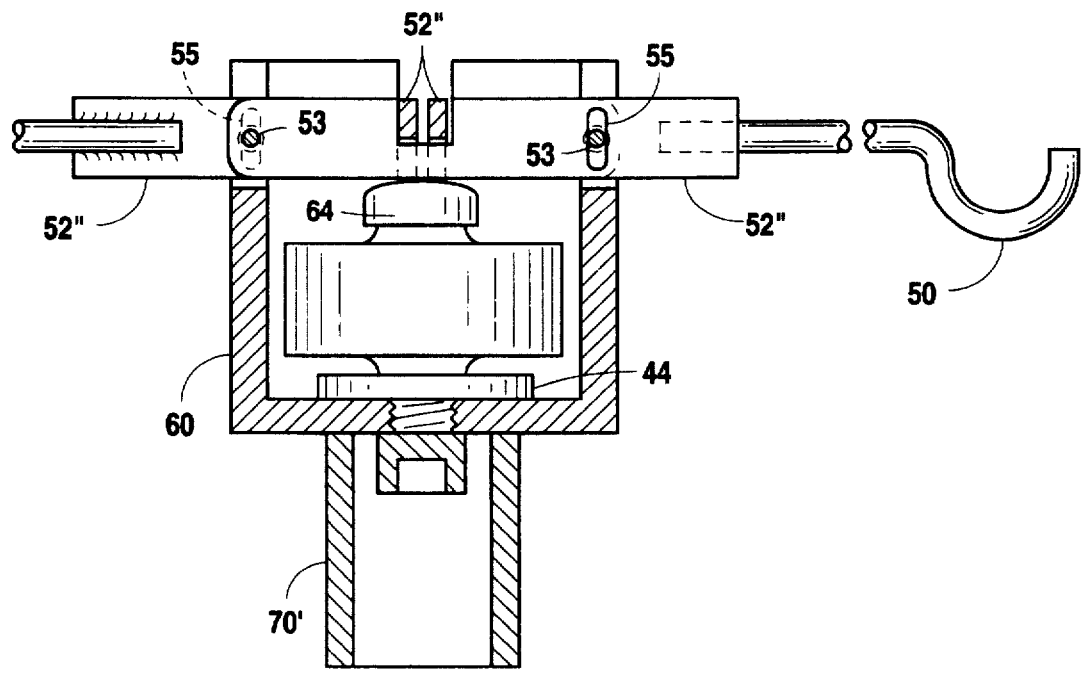
Figure 12E:
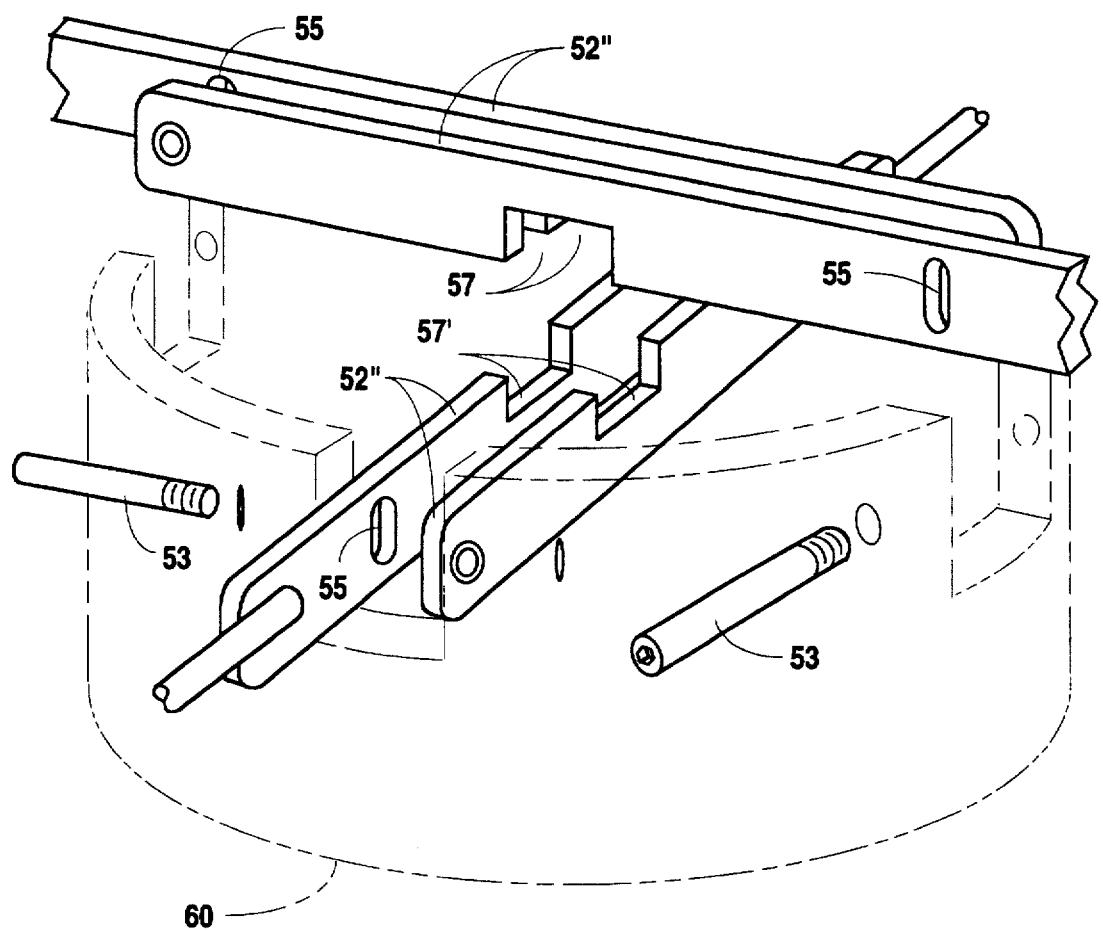

FIGS. 12A–C schematically illustrate examples of alternative preferred embodiments for weight-sensitive fluid supports. In FIGS. 12A–C, hook 50 is intended to suspend a fluid container (e.g., a plastic bag or a bottle made of glass or plastic). In FIGS. 12A and 12C, hook support arm 52 is preferably substantially rigid, being pivotally coupled through pivot bearing 54 to support arm frame 58 (FIG. 12A) or (as support arm 52") to support arm frame 60 (FIG. 12C). Each support arm 52,52" is supported at an intermediate point of its length by a force-sensitive device 64 which is preferably a solid-state load cell. Note that pivot shaft 53 (see FIG. 12C) preferably acts simultaneously to couple pivot 54 of support arm 52" to support arm frame 60 and also to limit the motion of a substantially parallel (but oppositely oriented) support arm 52". By its position within a substantially transverse elongated oversized slot 55 in the oppositely oriented support arm 52", pivot shaft 53 allows only limited upward motion of the oppositely oriented support arm 52", but does not interfere with the support arm's bearing on load cell 64. Note that in the configuration illustrated in FIGS. 12C–E, each support arm 52" bears eccentrically on load cell 64. This is in contrast to the condition of substantially concentric loading of load cell 64 by a single support arm 52 as illustrated in FIG. 12A. The degree of eccentric load cell loading by substantially parallel and oppositely oriented support arms 52" can be reduced by reducing the arm thickness and/or the spacing between portions of substantially parallel arms 52" proximate to notches 57, 57' because it is these proximate portions which bear on load cell 64. Note that if it is desirable to ensure individual contact of all support arms 52" with load cell 64 in the embodiment of FIG. 12C, notches 57, 57' must be sufficiently deep to avoid contact between any two notches 57, 57'. In certain preferred embodiments, however, individual support arm contact with load cell 64 is not required, and notches 57,57' can be more shallow so that each notch 57 bears on at least one notch 57' simultaneously with or instead of bearing on load cell 64. In any case, support arms 52,52', 52" should be substantially horizontal to ensure that signals from load cell 64 accurately indicate the weight suspended from any arm. For non-horizontal support arms 52, 52', 52", a corrected weight can be calculated by dividing the indicated weight by the cosine of each arm's angular deviation from the horizontal, analogous to the correction described above related to verticality compensation means. To further enhance accuracy, it is preferred that load cell 64 comprise means (for example, hydraulic coupling) to ensure that eccentrically applied loads are substantially accurately represented in a signal indicative of the load applied to the load cell.

In FIG. 12B, hook support arm 52' is preferably substantially rigidly coupled to support arm frame 58' and angle brace 56, but may deflect under load slightly due to bending which is sensed by strain gage 62. Either force-sensitive device 64 or strain gage 62 may be chosen in preferred embodiments to produce a source weight signal indicative of fluid source weight.

Support arm frames 58, 58' can be mounted on a wall, pole, cabinet, rack, or other suitable surface, with signals from pressure-sensitive device 64 and/or strain gage 62 being preferably being coupled to computing means 35 through one or more wires (not shown) or through infrared transmitter 63. In the latter case, transmitter 63 will preferably comprise a commercially available battery-powered infrared transmitter (analogous to those used to control television sets and other electrical devices) capable of transmitting an encoded version of the signals from force-sensitive device 64 and/or strain gage 62 using methods well-known to those of skill in the art. Note that weight-sensitive fluid support means may comprise one or more of the weight-sensitive fluid supports of the type schematically illustrated in FIGS. 12A–C. When a plurality of fluid supports is used, processor 34 is programmed to serially poll the individual fluid supports to obtain individual signals which may be combined (preferably summed) to form a signal indicative of (total) fluid source weight.

Figure 9:
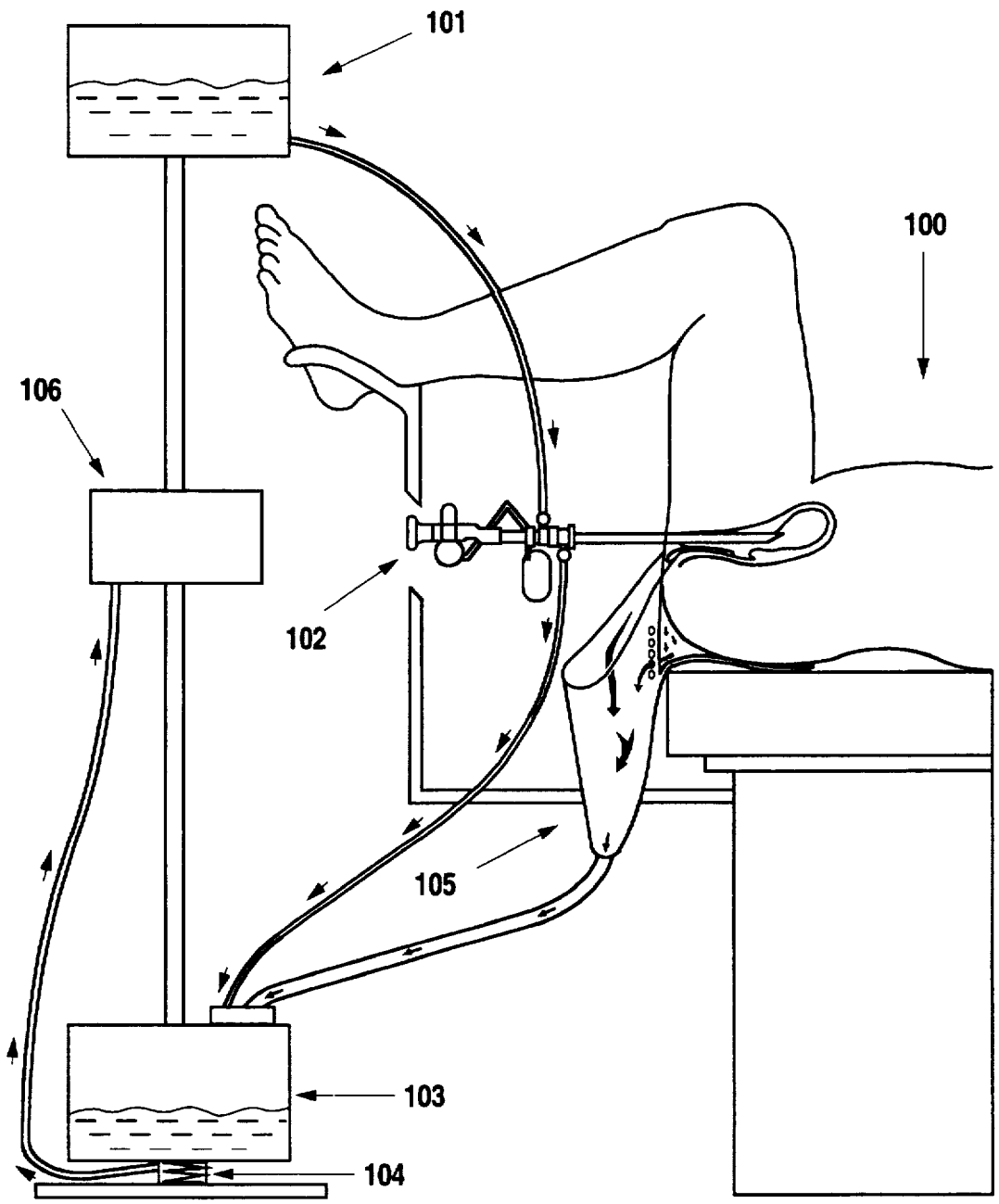
FIG. 9 schematically illustrates use of the present invention wherein fluid outflow from the fluid source is substantially equal to fluid inflow to the collection device, causing no alarm.
Figure 10:
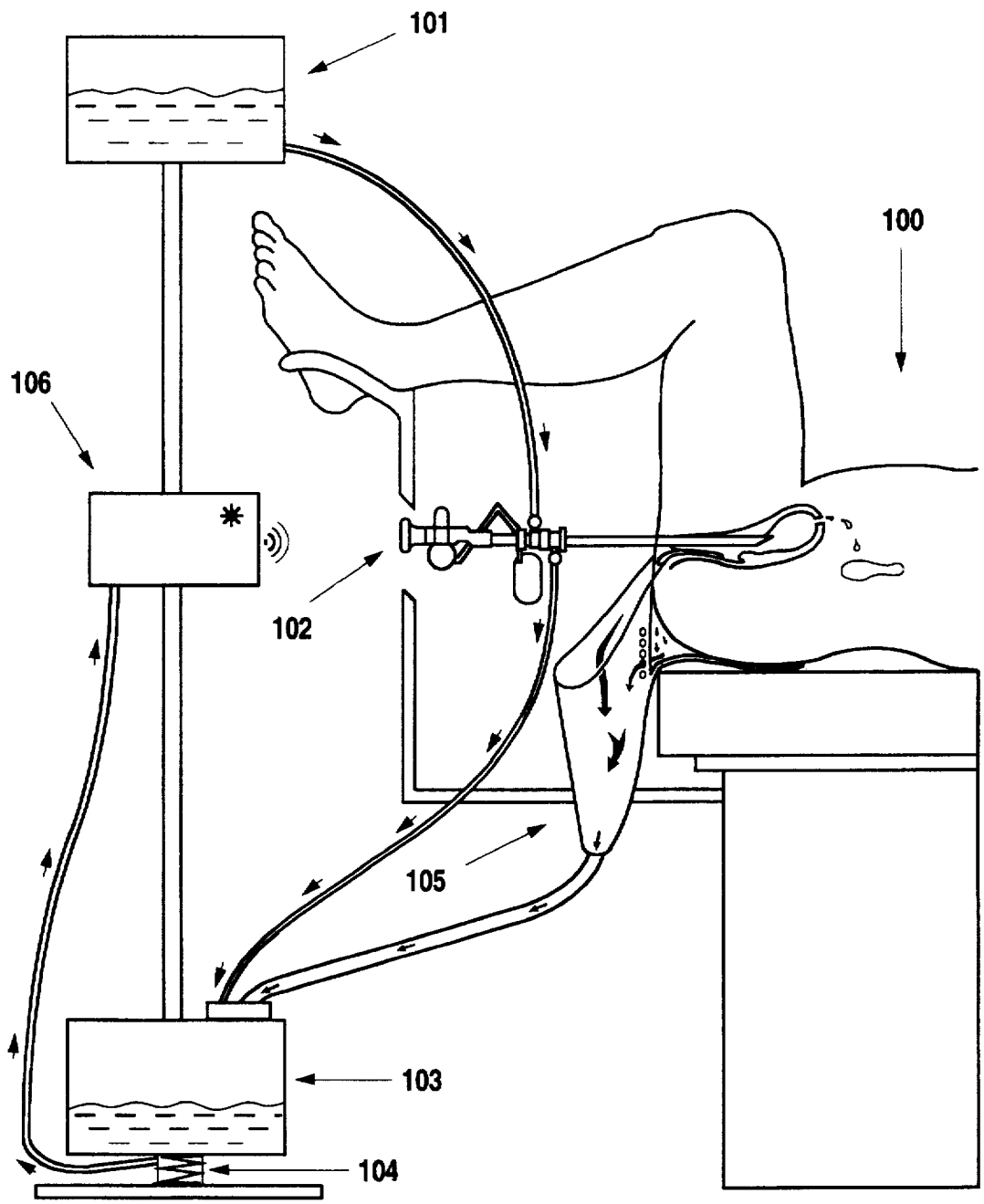
FIG. 10 schematically illustrates use of the present invention wherein fluid outflow from the fluid source is substantially greater than fluid inflow to the collection device, causing an alarm.

FIGS. 9 and 10 schematically indicate how an embodiment of the present invention analogous to that in FIG. 1 would work in practice. Irrigation fluid from source 101 flows by gravity to endoscope 102 which is inserted in patient 100. Waste irrigation fluid flows by gravity from endoscope 102 and from patient 100 (via fluid collection drape 105) to waste fluid collector 103. The combined weight of fluid source 101 and fluid collector 103 bears on weight-sensitive device 104, which transmits signals processor/display/alarm unit 106. When signals from device 104 indicate that total fluid weight is not changing significantly over time, this means that whatever fluid leaves the source is returned to the waste container and none is being absorbed by the patient so no alarm is set by unit 106 (see FIG. 9). On the other hand, if significantly less fluid is returned to the waste container than was removed from the fluid source, the total supported weight sensed by device 104 will significantly decline and an alarm will be set by unit 106 (see FIG. 10).

What is claimed is:

1. A surgical fluid monitor, comprising at least one weight-sensitive fluid source support for simultaneously suspending and weighing a fluid source and producing a fluid source weight signal indicative of fluid source weight;

at least one weight-sensitive waste fluid collector support for simultaneously suspending and weighing a waste fluid collector and producing a waste fluid collector weight signal indicative of waste fluid collector weight;

verticality compensation means to correct indicated fluid source weight and fluid collector weight;

computing means coupled to said verticality compensation means, to said fluid source weight signal, and to said waste fluid collector weight signal for calculating an estimated fluid absorbed value, and for producing a display signal indicative of a corrected estimated fluid absorbed value; and display means coupled to said computing means for transducing for human observation a display signal indicative of a corrected estimated fluid absorbed value.

2. The surgical fluid monitor of claim 1 wherein said at least one weight-sensitive fluid support and said weight-sensitive waste fluid collector support comprise at least one solid-state load cell.

3. The surgical fluid monitor of claim 2 further comprising a shock-absorbing spacer in-line with said solid-state load cell.

4. The surgical fluid monitor of claim 1 wherein said display means comprises a digital readout.

5. The surgical fluid monitor of claim 1 wherein said display means comprises a computer monitor screen.

6. The surgical fluid monitor of claim 1 wherein said computing means coupling comprises wireless means.

7. The surgical fluid monitor of claim 6 wherein said wireless means comprises a radio transmitter and receiver.

8. The surgical fluid monitor of claim 6 wherein said wireless means comprises an infrared transmitter and receiver.

9. The surgical fluid monitor of claim 6 wherein said wireless means is battery-powered.

10. The surgical fluid monitor of claim 1, additionally comprising at least one anti-rotation device.

11. A surgical fluid monitor, comprising at least one weight-sensitive fluid source support for simultaneously suspending and weighing a fluid source and producing a fluid source weight signal indicative of fluid source weight;

a weight-sensitive waste fluid collector support for simultaneously suspending and weighing a waste fluid collector and producing a waste fluid collector weight signal indicative of waste fluid collector weight;

at least one anti-rotation device coupled to said fluid source support and to said fluid collector support;

computing means coupled to said fluid source weight signal, and to said waste fluid collector weight signal for calculating an estimated fluid absorbed value, and for producing a display signal indicative of an estimated fluid absorbed value; and display means coupled to said computing means for transducing for human observation a display signal indicative of an estimated fluid absorbed value.

12. A weight-sensitive fluid source support, comprising at least one support arm, each said support arm having a first end, a second end, and a fulcrum contact point between said first end and said second end, said first end comprising a hook for supporting a weight load, and said second end comprising a pivot bearing about which said support arm can rotate;

a support arm frame, comprising at least one pivot bearing shaft for reversibly coupling each said support arm pivot bearing so that said support arm can rotate about said at least one pivot bearing shaft;

a force-sensitive device between each said fulcrum contact point and said support arm frame, said force-sensitive device experiencing a substantially compressive load when said support arm supports a weight load.

13. The weight-sensitive fluid source support of claim 12, comprising at least one pair of substantially parallel, oppositely oriented support arms.

14. The weight-sensitive fluid source support of claim 13, comprising two pairs of substantially parallel, oppositely oriented support arms.

15. A surgical fluid monitor, comprising at least one passive fluid source hook for suspending a fluid source;

at least one waste fluid collector bracket for supporting a waste fluid collector;

a weight-sensitive fluid support column for simultaneously supporting said at least one passive fluid source hook and said at least one waste fluid collector bracket and for producing a combined weight signal indicative of a sum of weight suspended from said at least one passive fluid source hook plus weight supported by said at least one waste fluid collector bracket;

verticality compensation means to correct indicated fluid source weight and fluid collector weight;

computing means coupled to said verticality compensation means and to said weight-sensitive fluid support column combined weight signal for calculating an estimated fluid absorbed value, and for producing a display signal indicative of a corrected estimated fluid absorbed value; and display means coupled to said computing means for transducing for human observation a display signal indicative of a corrected estimated fluid absorbed value.

* * * * *

REEXAMINATION CERTIFICATE (3551th)
United States Patent [19]
Vancaillie et al.

[11] B1 5,522,805
[45] Certificate Issued Jun. 16, 1998

[54] SURGICAL FLUID MONITOR

[75] Inventors: Thierry G. Vancaillie, San Antonio, Tex.; Robert K. Mitchiner, Longmont; David W. Newton, Boulder, both of Colo.

[73] Assignee: Aquintel, Inc., Longmont, Colo.

Reexamination Request:
No. 90/004,671, Jun. 12, 1997

Reexamination Certificate for:
Patent No.: 5,522,805
Issued: Jun. 4, 1996
Appl. No.: 484,877
Filed: Jun. 7, 1995

Related U.S. Application Data

[63] Continuation-in-part of Ser. No. 237,350, May 3, 1994, Pat. No. 5,492,537.

[51] Int. Cl.$^6$ .................................................. A61M 5/00
[52] U.S. Cl. ........................... 604/246; 604/65; 128/760
[58] Field of Search ........................... 604/65–67, 4, 604/31, 246; 128/760, 766; 364/413.01, 413.02

[56] References Cited

U.S. PATENT DOCUMENTS

| | | | |
|---|---|---|---|
| 3,410,268 | 11/1968 | Leucci | 128/227 |
| 3,992,706 | 11/1976 | Tunney et al. | 340/239 |
| 4,261,360 | 4/1981 | Perez | 128/230 |
| 4,299,705 | 11/1981 | Russel | 210/647 |
| 4,412,917 | 11/1983 | Ahjopalo | 210/104 |
| 4,449,538 | 5/1984 | Corbitt et al. | 128/760 |
| 4,457,750 | 7/1984 | Hill | 604/65 |
| 4,493,693 | 1/1985 | Bilstad et al. | 604/6 |
| 4,684,460 | 8/1987 | Issautier | 210/90 |
| 4,728,433 | 3/1988 | Buck et al. | 210/646 |
| 4,767,399 | 8/1988 | Bollish | 604/5 |
| 4,769,132 | 9/1988 | Patono | 210/86 |
| 4,793,362 | 12/1988 | Tedner | 128/734 |
| 4,795,424 | 1/1989 | Burner | 604/30 |
| 4,902,276 | 2/1990 | Zakko | 604/28 |
| 4,971,700 | 11/1990 | Tauji et al. | 210/647 |
| 4,990,258 | 2/1991 | Bjare et al. | 210/647 |
| 4,994,026 | 2/1991 | Fecondini | 604/29 |
| 4,995,268 | 2/1991 | Ash et al. | 73/861.05 |
| 5,003,296 | 3/1991 | Lee | 340/618 |
| 5,004,459 | 4/1991 | Peabody et al. | 604/29 |
| 5,112,298 | 5/1992 | Prince et al. | 604/6 |
| 5,135,485 | 8/1992 | Cohen . | |
| 5,152,746 | 10/1992 | Atkinson et al. | 604/31 |
| 5,178,606 | 1/1993 | Ognier et al. | 604/31 |
| 5,211,849 | 5/1993 | Kitaevich et al. | 210/645 |
| 5,234,608 | 8/1993 | Duff | 210/806 |
| 5,312,334 | 5/1994 | Hara et al. | 604/65 |
| 5,328,478 | 7/1994 | McVay | 604/147 |
| 5,344,568 | 9/1994 | Kitaevich et al. | 210/645 |
| 5,372,709 | 12/1994 | Hood | 210/90 |
| 5,376,070 | 12/1994 | Purvis et al. | 604/31 |
| 5,421,812 | 6/1995 | Langley et al. | 604/4 |
| 5,437,629 | 8/1995 | Goldrath | 604/21 |
| 5,445,610 | 8/1995 | Evert | 604/29 |
| 5,458,567 | 10/1995 | Cathcart | 604/4 |
| 5,503,626 | 4/1996 | Goldrath | 604/65 |
| 5,586,973 | 12/1996 | Lemaire et al. | 604/19 |

FOREIGN PATENT DOCUMENTS

WO 92/18049  10/1992  WIPO .

OTHER PUBLICATIONS

McDonald, H.P. "An Automatic Peritoneal Dialysis Machine for Hospital or Home Peritoneal Dialysis: Preliminary Report", Trans. Amer. Soc. Artif. Int. Organs, 15:108–113, 1969.

*Primary Examiner*—Corrine M. McDermott

[57] ABSTRACT

A monitor to provide substantially real-time estimates of fluid absorbed by a patient during an endoscopic surgical procedure. The monitor comprises means for weighing fluid administered to the patient intravenously, as well as that introduced through the endoscope for irrigation purposes. In addition, means are provided for weighing fluid recovered from the patient, the endoscope, and the surgical drapes. The total weight of fluid administered, reduced by subtracting the total weight of fluid recovered, comprises the calculated fluid absorbed. Through manual entries and/or switch settings, computing means maintain totals of fluid administered and fluid collected even as fluid sources are replaced and the fluid collector is emptied. Optional verticality compensation means and anti-rotation devices are included.

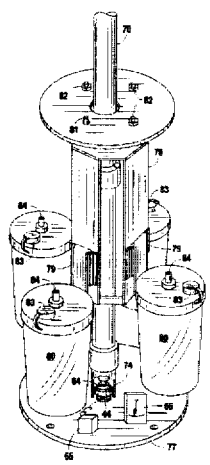

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

* * * * *